United States Patent [19]

Charowsky et al.

[11] Patent Number: 4,998,538
[45] Date of Patent: Mar. 12, 1991

[54] MEDICAL DRAPE FOR LASER SURGERY

[76] Inventors: Deborah A. Charowsky; Harry P. Charowsky, both of 45047 SE. 166th St., North Bend, Wash. 98045

[21] Appl. No.: 398,712

[22] Filed: Aug. 25, 1989

[51] Int. Cl.⁵ .............................................. A61B 19/12
[52] U.S. Cl. .................................... 128/856; 128/917; 128/863
[58] Field of Search ............... 128/849, 851, 853, 854, 128/855, 856, 846, 917, 847, 863; 250/516.1, 517.1, 519.1

[56] References Cited

U.S. PATENT DOCUMENTS

| | | | |
|---|---|---|---|
| 3,763,857 | 10/1973 | Schrading | 128/853 |
| 3,850,172 | 11/1974 | Cazalis | 128/856 X |
| 4,122,848 | 10/1978 | Carpel | 128/849 X |
| 4,275,719 | 6/1981 | Malier | 128/849 X |
| 4,581,538 | 4/1986 | Lenhart | 250/519.1 |
| 4,601,286 | 7/1986 | Kaufman | 128/853 X |
| 4,604,998 | 8/1986 | Bellina | 250/519.1 X |
| 4,865,049 | 9/1989 | Gatti | 128/849 |
| 4,867,177 | 9/1989 | Urheim | 128/849 |

FOREIGN PATENT DOCUMENTS

| | | | |
|---|---|---|---|
| 2313201 | 9/1974 | Fed. Rep. of Germany | 250/519.1 |
| 247426 | 7/1969 | U.S.S.R. | 250/515.1 |
| 2110986 | 6/1983 | United Kingdom | 250/515.1 |

Primary Examiner—Robert A. Hafer
Assistant Examiner—Kevin G. Rooney
Attorney, Agent, or Firm—Chernoff, Vilhauer, McClung & Stenzel

[57] ABSTRACT

A disposable medical drape adapted for use in laser surgery is configured to form an enclosure, acting as an emission barrier, between the medical laser and the patient tissue to be removed so as to contain, within the enclosure, materials present in the laser plume. The drape includes a floor having an opening therein which defines the target area of patient tissue. The floor includes moisture-absorbent material which is premoistened to protect the patient from errant laser shots. The underside of the floor includes an adhesive material for fixing the floor of the drape directly to the skin of the patient. The drape includes flexible transparent walls which extend from the floor of the drape to the medical laser, the walls including stiffening rings to define an obstruction-free corridor for the laser beam. The walls of the drape are gathered around the barrel of the medical laser so as to prevent emissions at that juncture. The walls of the drape include suction ports adapted to be used with evacuation equipment for removing laser plume materials from the enclosure and creating a negative pressure therein. The walls of the drape also provide access to the patient tissue. The material of the drape is nonflammable.

21 Claims, 1 Drawing Sheet

MEDICAL DRAPE FOR LASER SURGERY

BACKGROUND OF THE INVENTION

This invention relates to a disposable medical drape, and particularly to such a drape for use in laser surgery to act as an emission barrier to protect the environment of the operating room from contamination by airborne materials which result from laser surgery.

While there are many new applications for laser surgery, and its advantages over conventional surgery in particular situations are substantial, there is growing concern about contamination by emissions contained in the laser plume. In laser surgery, the laser beam removes patient tissue by vaporization. The patient tissue is heated by the laser beam until the moisture in the tissue causes it to vaporize and/or explode or until the tissue burns. The procedure creates an plume of material which can include patient tissue, patient fluids, smoke and other gases. Such plumes can contain live cells and active viruses. Applicants are aware of instances where live viruses have been discovered in the vocal chords and on the forearms of the surgeon after laser surgery. With increased awareness of such highly communicable diseases as AIDS, such contamination is highly undesirable.

Conventional medical drapes, typically made of cotton cloth, are unsuited to laser surgery. They are porous, allowing the laser plume to pass through the drape; they are flammable, and may catch fire if the laser beam strikes the drape; and they are opaque, interfering with the view of the medical personnel.

Another concern with laser surgery is to protect the patient from exposure to the surgical laser beam except in the precise area where tissue is to be removed. An errant laser shot by a surgeon could penetrate conventional drapes and burn the patient or result in unwanted tissue removal.

What is needed is a transparent, non-flammable drape that will not interfere with the process of laser surgery, that will protect the patient from unwanted tissue removal, and will serve as an emission barrier to contain the laser plume.

SUMMARY OF THE INVENTION

The medical drape of the present invention provides an enclosure which extends between the medical laser and the patient tissue to be removed and acts as a barrier to retain, in the enclosed space, the laser plume resulting from laser surgery. The enclosure formed by the drape has an opening which encircles the patient tissue to be removed. According to the exemplary embodiments described herein, the portion of the enclosure which is adjacent to the opening includes adhesive for attaching the enclosure directly to the patient's skin, and moisture absorbent material, which when moistened will prevent the laser beam from immediately penetrating the drape and harming the patient. Preferably, the portion of the enclosure extending between the patient and the laser is nonflammable, and transparent so that operating room personnel may view the tissue to be removed. According to an exemplary embodiment, the drape is used in combination with some sort of vacuum evacuation equipment to remove the laser plume from the enclosure and create a negative pressure within the enclosure to prevent escape of plume materials.

Accordingly, it is the primary objective of the present invention to provide a new medical drape for use in laser surgery.

It is a principal objective to provide such a drape which encloses the patient tissue and the laser and acts as a barrier to prevent emissions which are contained in the laser plume from contaminating the operating room.

It is a further objective to provide such a drape that is compatible with equipment for evacuating the laser plume from the enclosure created by the drape.

It is another objective to provide such a drape that is non-flammable.

It is a further objective to provide a drape which includes means for attaching the drape to the patient so that the target area of patient tissue to be removed is defined.

It is a related objective of the present invention to provide such a drape which includes means for protecting the patient from errant laser beams.

It is a further objective of the present invention to provide such a drape which is at least partially transparent so that the patient tissue may be observed by operating room personnel.

It is another objective to provide such a drape which permits access into the enclosed space created by the drape.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
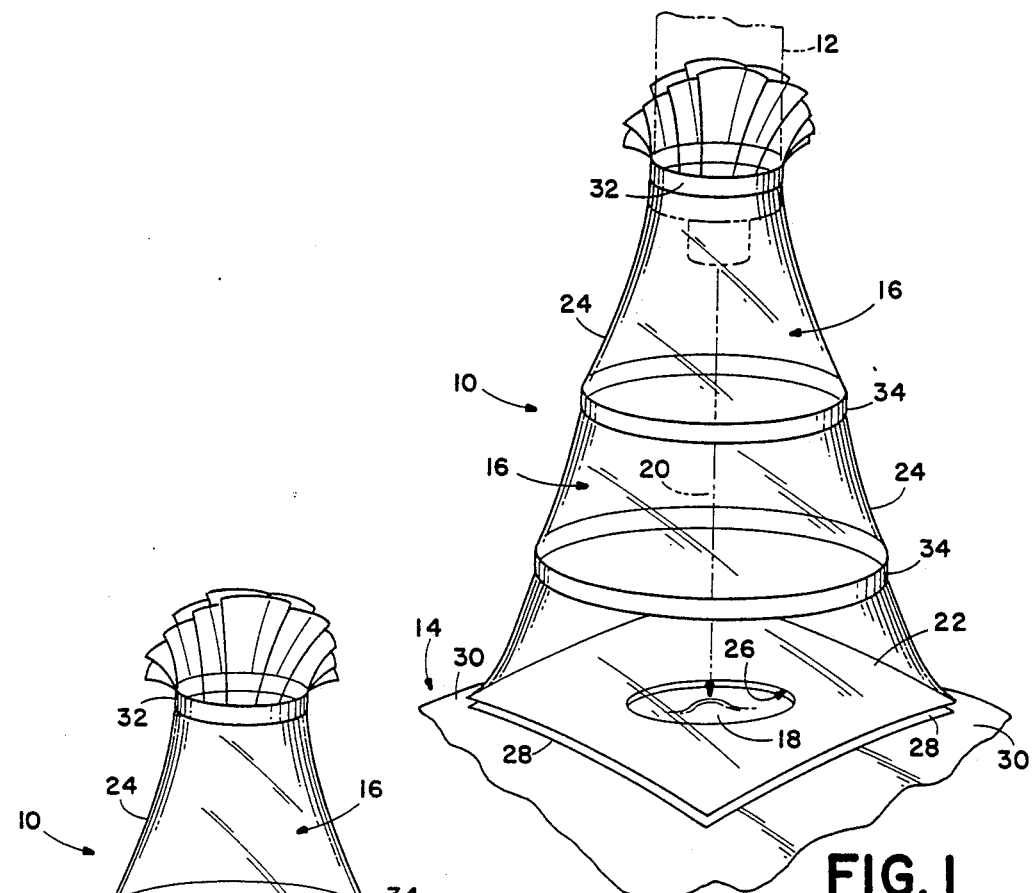
FIG. 1 is a perspective view of an exemplary embodiment of the drape of the present invention.

Referring to the exemplary embodiment shown in FIG. 1, the drape 10 of the present invention is shown in relation to a medical laser 12 and a patient 14, the drape creating an enclosed space 16 extending between the laser 12 and the patient tissue 18 which is to be removed by the laser, the enclosed space defining a corridor through which the laser beam 20 may pass unobstructed.

The drape includes a floor 22 and walls 24. The floor includes a central opening 26 which encircles the patient tissue to be removed and defines the target area of the laser. In the exemplary embodiment of FIG. 1, the floor 22 includes a subfloor 28 which is attached to the floor. The underside of the subfloor includes an adhesive for causing the subfloor to adhere directly to the skin 30 of the patient. In the exemplary embodiment it is contemplated that the floor and subfloor will be laminated together into a two-ply assembly. FIG. 1 shows them peeled apart to aid in the description of the embodiment.

The surface of the floor which faces the laser includes protective means for impeding penetration of the floor by an errant laser beam which fails to strike the target area defined by the opening in the floor. One example of such protective means is to include non-flammable, moisture-absorbent material in the floor and moisten it prior to the laser procedure. The moistened material will prevent a laser beam which strikes the area of the floor proximate the opening from immediately penetrating the floor and burning the patient. Of course, if the laser beam is allowed to continue to strike the same area of the moistened floor, it will vaporize the moisture and eventually penetrate the floor. In the embodiment discussed above, it may be preferable that adhesive of the subfloor be water-resistant so that moistening the floor does not cause the subfloor to detach from the patient. However, if there is some type of moisture-proof barrier between the absorbent material and the adhesive, it would not be necessary to use moisture-resistant adhesive. Applicants are aware of a suitable, non-flammable, moisture absorbent material used in SURGIKOS drapes made by Johnson & Johnson. Other types of protective means which may be incorporated into the floor or the drape are Kimberly Clark's CONVERTORS.

With the floor attached to the patient as shown in FIG. 1, the walls extend out from the floor toward the laser where the walls are attached to the laser so as to substantially complete, in cooperation with the floor, enclosure of the laser and patient tissue. The walls define an obstruction-free corridor between the laser and the patient so that the laser beam passes centrally through the corridor.

The walls of the drape may be supportably attached to the laser by any number of suitable means. The exemplary embodiment shows them gathered around the barrel of the laser with a retaining band 32. Ties, adhesive tapes, elastic bands, and the like are all suitable devices to the extent that they serve to prevent escape of emissions around the laser itself and supportably attach the drape to the laser.

The exemplary drape shown in FIG. 1 is preferably made of flexible, non-flammable material. Further, the walls 24 are transparent so as to not block illumination of the patient tissue to be removed and permit the operating room personnel to have a clear view of the target area and patient tissue. The drape should be non-flammable so that if any portion of the drape does inadvertently become positioned in the path of the laser beam, the drape will not catch fire. With respect to the walls of the drape, applicants are aware of a transparent, flexible, non-flammable material which is used for oven bags for roasting meats and other foods, of the type manufactured by the Reynolds Company.

Since the purpose of the drape is to contain the laser plume, the material of the drape should be sufficiently nonporous to achieve this result. As will be explained more fully below, the drape may be used in combination with evacuation equipment to draw the laser plume out of the enclosure defined by the drape and create a negative pressure within the enclosure. When used in such combination, the material may be more porous than if it is used without any type of evacuation equipment. Preferably, the drape itself, or the drape in combination with the evacuation equipment, should prevent escape of particles which are greater than 0.3 microns in size.

Figure 2:
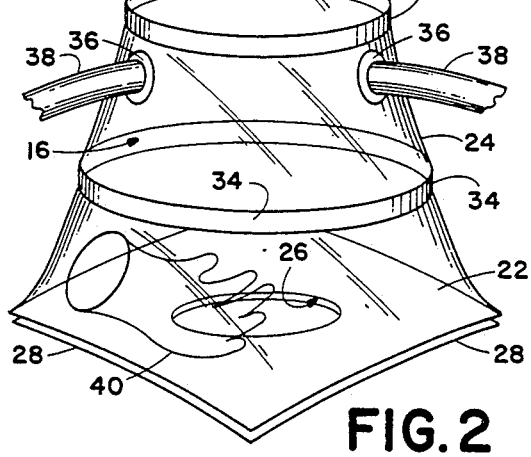
FIG. 2 is a perspective view of an alternative embodiment of the drape having vacuum hoses and an access glove.

Flexibility of the drape material is preferred so that the drape can be adapted to be used with almost any portion of the human anatomy and permit various positioning of the laser with respect to the patient. Although the exemplary embodiments of FIGS. 1 and 2 show the patient beneath the laser, the drape is capable of being used in other configurations. In this respect, it will be appreciated that the drape has been described herein as it would be configured when employed in an environment containing a patient and a laser. Apart from such an environment, the drape, due to its flexible nature, may assume other shapes.

Due to the flexibility of the drape, and the critical necessity to keep the drape out of the laser path, the exemplary embodiment shown in FIG. 1 includes structural members in the form of semi-rigid rings 34 incorporated into the walls. These rings help to define the enclosure formed by the drape and form the corridor through which the laser beam passes.

The rings are particularly important in the embodiment shown in FIG. 2 which is equipped with suction ports 36 adapted to receive and retain vacuum hoses 38. The vacuum hoses communicate with evacuation equipment such as a suction pump to draw the laser plume out of the enclosure formed by the drape and create a negative pressure—that is a pressure below ambient pressure—within the enclosure. With a negative pressure within the enclosure, the rings are instrumental in preventing the flexible drape from collapsing inwardly and obstructing the laser beam. The suction ports may be plugged when the drape is not used in combination with evacuation equipment.

The alternative embodiment of FIG. 2 also shows an access glove 40 incorporated into the walls of the drape so that the surgeon or other operating room personnel may have access to the patient tissue within the enclosure without breaching the barrier formed by the drape. Actually, it is not necessary or desired that the enclosure formed by the drape be air-tight since the negative pressure caused by the suction pump will substantially prevent the laser plume from escaping from the enclosure except through the suction ports. Accordingly, another embodiment of the drape may merely employ access slits (not shown) in the walls and/or floor rather than the access glove of FIG. 2.

Although the drape of the present invention has been described in connection with its application to laser surgery, it also has application in electrosurgery such as electrocautery procedures wherein a blood vessel is closed by cauterizing the vessel with an electrically charged instrument, rather than closing the vessel with a suture. Such a procedure also generates smoke and vapors which could be contained by applicants' drape.

The drape may also be attached to the patient by means other than the adhesive floor described above. For example, ties, adhesive tapes, or elastic cuffs would all be suitable to attach the drape to the patient, or to attach the drape to other drapes which are applied to the patient, so long as they serve to fix the opening so as to encircle the tissue to be removed. It would be within the concept of the present invention to use a drape having a tie or an elastic cuff which could be placed on a patient's foot, for example, when removing plantar warts.

Finally, although the drape has been described with a central opening formed in the floor, it is not necessary or desirable that the drape, as manufactured and supplied, include such an opening. Indeed, it may be more advantageous in certain circumstances to have the operating room personnel create an opening in the floor, by cutting out a portion of the floor, to fit a particular situation.

The terms and expressions which have been employed in the foregoing abstract and specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A medical drape for use in a medical procedure wherein a laser is employed to remove tissue from a patient, said drape comprising:
   (a) an enclosure extending between the laser and the patient tissue to be removed, said enclosure defining a substantially enclosed space between the laser and the patient tissue;
   (b) said enclosure including target area boundary means for encircling a target area of patient tissue to be removed, said target area boundary means defining an opening in said enclosure; and
   (c) said enclosure including containment means for substantially retaining, in said enclosed space, material resulting from laser removal of patient tissue.

2. The drape of claim 1 wherein said enclosure includes fastening means proximate said opening for attaching a portion of said enclosure which is adjacent said opening to said patient, and for fixing said opening so as to encircle said target area, said portion of said enclosure which is adjacent to said opening defining a floor of said enclosed space.

3. The drape of claim 2 wherein said fastening means includes adhesive means for causing said floor to adhere to the skin of the patient.

4. The drape of claim 1 wherein a portion of said enclosure which is adjacent said opening includes protective means for impeding penetration of said enclosure by an errant laser beam which fails to strike said target area.

5. The drape of claim 4 wherein said protective means includes moisture absorbent means for absorbing and retaining moisture in said portion of said enclosure adjacent said opening.

6. The drape of claim 1 wherein a portion of said enclosure adjacent said opening defines a floor of said enclosed space, said floor having an upper surface facing said enclosed space and a lower surface facing away from said enclosed space, said lower surface of said floor including fastening means for attaching said floor to said patient and for fixing said opening so as to encircle said target area.

7. The drape of claim 6 wherein said upper surface of said floor includes protective means for impeding penetration of said floor by an errant laser beam which fails to strike said target area.

8. The drape of claim 7 wherein said protective means includes moisture absorbent means for absorbing and retaining moisture in said floor, and said fastening means includes adhesive means for fastening said floor to the skin of the patient.

9. The drape of claim 1 wherein said enclosure includes attachment means proximate said laser for attaching said enclosure to said laser.

10. The drape of claim 1, further including structural support means attached to said enclosure for supporting said enclosure and preventing said enclosure from becoming interposed between the laser and said target area.

11. The drape of claim 1 wherein a portion of said enclosure is non-flammable.

12. The drape of claim 1 wherein a portion of said enclosure proximate the laser is constructed of flexible, substantially transparent material which will impede passage of particles through said enclosure.

13. The drape of claim 1 in combination with means for maintaining said substantially enclosed space at a pressure which is below ambient pressure.

14. The drape of claim 1 in combination with means for removing gases and airborne particles from within said enclosed space.

15. The drape of claim 1 wherein said enclosure means includes one or more aperture means apart from said opening for permitting access to said enclosed space.

16. The drape of claim 1 wherein the laser and said target area together define a straight laser beam path extending between the laser and said target area, said enclosure arranged so as to define a laser corridor whose approximate central axis is said laser beam path.

17. The drape of claim 16 wherein said enclosure includes semi-rigid structural means for shaping said enclosure so as to define said laser corridor.

18. A medical drape for use in a medical procedure wherein a laser is employed to remove tissue from a patient, said drape comprising a floor proximate the patient, said floor including opening means for surrounding the patient tissue to be removed, and an elongate sleeve having first and second ends defined by an endless sleeve wall, said floor attached to said first end of said sleeve so as to close said first end of said sleeve, said second end of said sleeve closed so that said sleeve and said floor together substantially define an enclosed space, said sleeve and said floor cooperating as containment means for retaining, in said enclosed space, material resulting from laser removal of patient tissue.

19. A method for containing emissions resulting from removal of patient tissue by laser beam, said method comprising providing an enclosure which defines an enclosed space extending between the laser and the patient tissue to be removed, said enclosure including opening means for encircling the patient tissue to be removed; affixing said enclosure to said patient so that said opening means encircles the patient tissue to be removed; and attaching said enclosure to the laser so that a laser beam from the laser has an unobstructed path to the patient tissue to be removed, said enclosure acting as containment means for retaining, in said enclosed space, material resulting from laser removal of patient tissue.

20. The method of claim 19, further including providing evacuation means for removing emissions from said enclosure and maintaining the pressure in said enclosure below ambient pressure so as to substantially prevent emissions from escaping from said enclosure except through said evacuation means.

21. The method of claim 19, further including providing a portion of said enclosure surrounding said opening means with moisture absorbent material and moistening said moisture absorbent material so that an errant laser beam which fails to strike the patient tissue to be removed does not penetrate said enclosure and burn the patient.

* * * * *